(12) United States Patent
Filipiak et al.

(10) Patent No.: US 11,039,911 B2
(45) Date of Patent: *Jun. 22, 2021

(54) MEDICAL DEVICE HAVING REMOVABLE DEPLOYMENT DEVICE AND AFFIXATION ELEMENT

(71) Applicant: ATRIUM MEDICAL CORPORATION, Merrimack, NH (US)

(72) Inventors: David Filipiak, Somerville, MA (US); Anthony R. Horton, Bedford, NH (US); Albert A. Lepage, Manchester, NH (US)

(73) Assignee: ATRIUM MEDICAL CORPORATION, Merrimack, NH (US)

( * ) Notice: Subject to any disclaimer, the term of this patent is extended or adjusted under 35 U.S.C. 154(b) by 139 days.

This patent is subject to a terminal disclaimer.

(21) Appl. No.: 16/171,003

(22) Filed: Oct. 25, 2018

(65) Prior Publication Data
US 2019/0060049 A1 Feb. 28, 2019

Related U.S. Application Data

(63) Continuation of application No. 14/878,091, filed on Oct. 8, 2015, now Pat. No. 10,136,983.

(51) Int. Cl.
*A61F 2/00* (2006.01)

(52) U.S. Cl.
CPC .... *A61F 2/0063* (2013.01); *A61F 2002/0072* (2013.01); *A61F 2210/0076* (2013.01); *A61F 2220/0025* (2013.01)

(58) Field of Classification Search
CPC ...... A61F 2002/0072; A61F 2210/0076; A61F 2220/0025; A61F 2/0063
See application file for complete search history.

(56) References Cited

U.S. PATENT DOCUMENTS

| 3,328,259 A | 6/1967 | Anderson |
| 5,480,436 A | 1/1996 | Bakker et al. |
| 5,634,931 A | 6/1997 | Kugel |

(Continued)

FOREIGN PATENT DOCUMENTS

| CN | 201879864 U | 6/2011 |
| CN | 104010601 A | 8/2014 |

(Continued)

OTHER PUBLICATIONS

Supplementary European Search Report dated May 21, 2019 during the prosecution of corresponding European Patent Application No. 15905952.6, 7 pages.

(Continued)

*Primary Examiner* — Kathleen S Holwerda
*Assistant Examiner* — Brooke Labranche
(74) *Attorney, Agent, or Firm* — Wesley Scott Ashton (57) ABSTRACT

A medical device including a first layer having an opening formed therein. A second layer is positioned with respect to the first layer to form a pocket therebetween. A support member is at least partially located in the pocket and reconfigurable for removal of the support member from the pocket via the opening. An affixation element located in the pocket between the support member and the second layer, and secured to the second layer. A method of implanting a medical device is also included.

20 Claims, 11 Drawing Sheets

(56) References Cited

U.S. PATENT DOCUMENTS

| | | |
|---|---|---|
| 6,548,081 B2 | 4/2003 | Sadozai et al. |
| 2004/0019360 A1 | 1/2004 | Farnsworth et al. |
| 2007/0299538 A1 | 12/2007 | Roeber |
| 2008/0077222 A1 | 3/2008 | Johnson et al. |
| 2009/0192530 A1 | 7/2009 | Adzich et al. |
| 2011/0224704 A1 | 9/2011 | Bailly .................. A61F 2/0063 606/151 |
| 2013/0103058 A1 | 4/2013 | Gobran |
| 2013/0267971 A1 | 10/2013 | Liu et al. |
| 2014/0025093 A1 | 1/2014 | Horton .................. A61F 2/0063 606/151 |
| 2014/0148827 A1 | 5/2014 | Odermatt et al. |
| 2015/0148824 A1 | 5/2015 | Horton et al. |
| 2015/0257866 A1 | 9/2015 | Filipiak et al. |

FOREIGN PATENT DOCUMENTS

| | | |
|---|---|---|
| CN | 104203123 A | 12/2014 |
| CN | 104220024 A | 12/2014 |
| CN | 104661616 A | 5/2015 |
| JP | 2005-534404 A | 11/2005 |
| JP | 2009-541011 A | 11/2009 |

OTHER PUBLICATIONS

Chinese Office Action and Chinese Search Report (with English translation) dated Oct. 8, 2019 during the prosecution of corresponding Chinese Patent Application No. 201580083615.8, 17 pages.

Japanese Office Action (with English translation) dated Jul. 16, 2019 during the prosecution of related Japanese Patent Application No. 2018-538518, 10 pages.

Office Action issued in counterpart Chinese Application No. 201580083615.8 dated Apr. 20, 2020, 10 pages.

Examination Report issued in counterpart Australian Application No. 2015411318 dated Jun. 16, 2020, 4 pages.

International Search Report and Written Opinion dated Dec. 31, 2015, issued in corresponding PCT Application No. PCT/US2015/054670, 10 pages.

Extended European Search Report in EP Application No. 13767588.0, dated Oct. 12, 2015, 6 pages.

Japanese Office Action (with English translation) dated Jan. 7, 2020 during the prosecution of corresponding Japanese Patent Application No. 2018-538518, 6 pages.

Non-Final Office Action issued in U.S. Appl. No. 15/817,018, dated Sep. 19, 2018.

Notification to Grant Patent Right and Search Report issued in CN Application No. 201580083615.8 dated Jul. 17, 2020 (7 pages).

Non-Final Office Action issued in U.S. Appl. No. 14/878,091 dated Jun. 1, 2017, 9 pages.

Final Office Action issued in U.S. Appl. No. 14/878,091 dated Oct. 2, 2017, 10 pages.

Non-Final Office Action issued in U.S. Appl. No. 14/878,091 dated Feb. 2, 2018, 9 pages.

International Preliminary Report on Patentability issued in International Application No. PCT/US2015/054670, 7 pages.

MEDICAL DEVICE HAVING REMOVABLE DEPLOYMENT DEVICE AND AFFIXATION ELEMENT

This application is a continuation application of U.S. patent application Ser. No. 14/878,091, which was filed on Oct. 8, 2015, and is now U.S. Pat. No. 10,136,983 B2. The disclosures of the above mentioned application and patent are hereby incorporated by reference in their entirety for all they disclose.

BACKGROUND

Prostheses are known in the medical device industry for the repair of hernias and other tissue structure defects. Various designs have been invented and commercialized to handle an increasing array of situations or to an increasing degree of efficacy. The industry would well receive additional advancements and alternates in this field.

SUMMARY

A medical device including a first layer having an opening formed therein. A second layer is positioned with respect to the first layer to form a pocket therebetween. A support member is at least partially located in the pocket and reconfigurable for removal of the support member from the pocket via the opening. An affixation element located in the pocket between the support member and the second layer, and secured to the second layer.

In one embodiment, the affixation element is secured to the second layer at a securement region, and the affixation element is secured to the second layer at a location separate from the securement region. In one embodiment, the affixation element is at least partially blocked from access through the opening when the support member is located in the pocket. In one embodiment, the affixation element is able to at least partially extend out from the pocket through the opening when the support member is removed from the pocket. In one embodiment, the affixation element is at least partially formed by a mesh material. In one embodiment, the medical device can be held against an anatomical structure by the support member when the support member is at least partially located within the pocket, and by the affixation element when the support member is fully or at least partially removed from the pocket.

In one embodiment, the pocket is delimited by an underside surface of the first layer and an upper surface of the second layer. T In one embodiment, a tensile force is able to be applied to the medical device at (i) the underside surface of the first layer by the support member and (ii) at the upper surface of the second layer by the affixation element.

In one embodiment, the support member has at least one dimension that is larger than a corresponding dimension of the opening to frustrate or impede removal of the support member from the pocket. In one embodiment, the support member is reconfigurable in response to a tensile force applied to the support member in order to remove the support member from the pocket via the opening. In one embodiment, the affixation element includes one or more tabs extending from a hub and the hub is affixed to the second layer. In one embodiment, the affixation element has a circular shape or a polygonal shape.

In one embodiment, the affixation element includes separate fingers or tabs that are secured individually to the second layer. In one embodiment, the affixation element is attached to the second layer at a region located generally proximate to a center of the medical device relative to a position of the affixation element. In one embodiment, the affixation element is attached to the second layer at a region located generally radially outwardly from a center of the medical device relative to a position of the affixation element.

A method of implanting a medical device is also included. The method includes positioning a medical device against an anatomical structure by exerting a tensile force on a support member of the medical device, the support member at least partially located in a pocket formed between a first layer and a second layer of the medical device secured to each other and extending outward from the pocket through an opening in the first layer, removing the support member from the pocket through the opening in the first layer in order to provide access through the opening to an affixation element located in the pocket and secured to the second layer, and securing the medical device to the anatomical structure via the affixation element. The method of claim 1, wherein removing the support member from the pocket includes reconfiguring the support member via the tensile force to fit the support member through the opening.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments of the disclosed apparatus and method are presented herein by way of exemplification and not limitation with reference to the Figures. It is noted at the outset that the term "may" is intended to impart optionality of features, parts, materials, components, or composition of the embodiments disclosed below.

Figure 1:
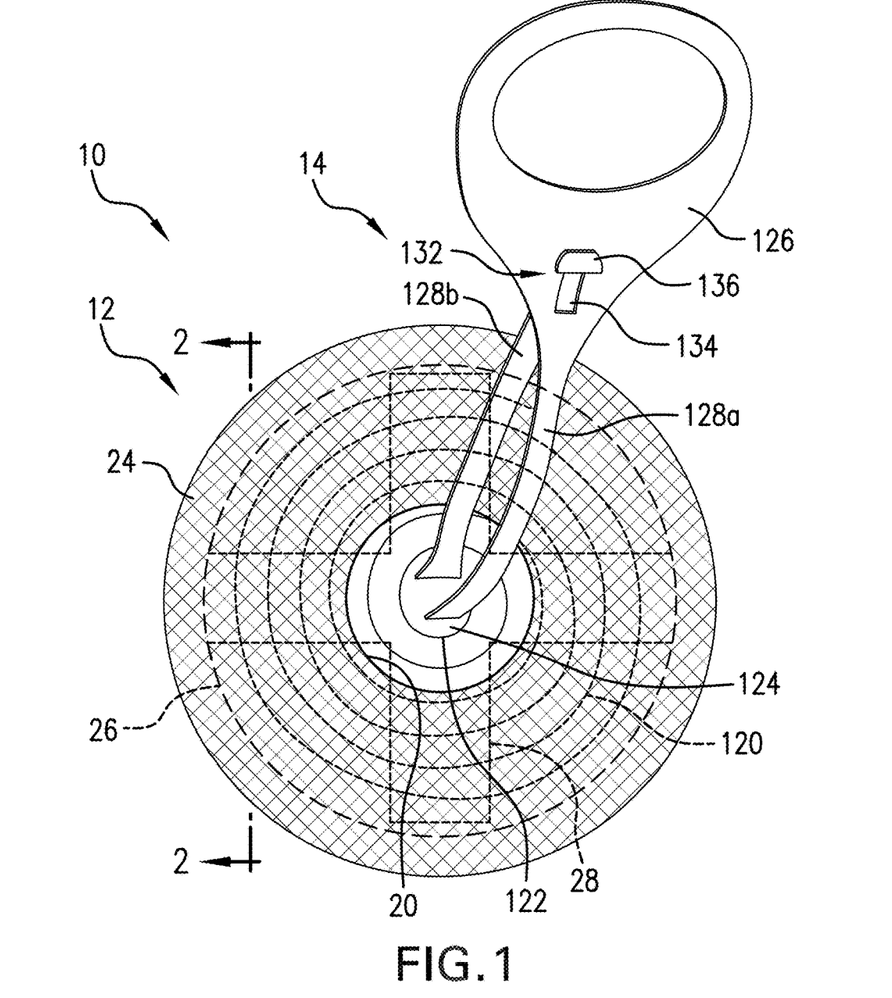
FIG. 1 is a perspective view of a medical device according to one embodiment disclosed herein.
Figure 2:
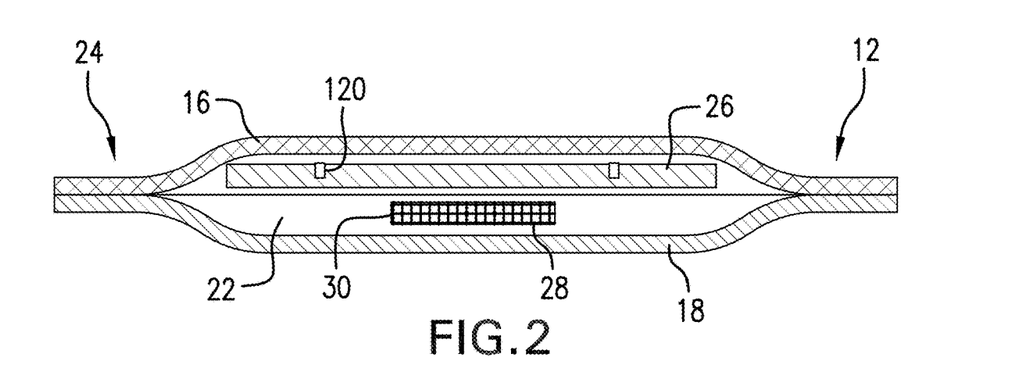
FIG. 2 is a cross-sectional view of the medical device of FIG. 1 taken generally along sectional line 2-2.
Figure 3:
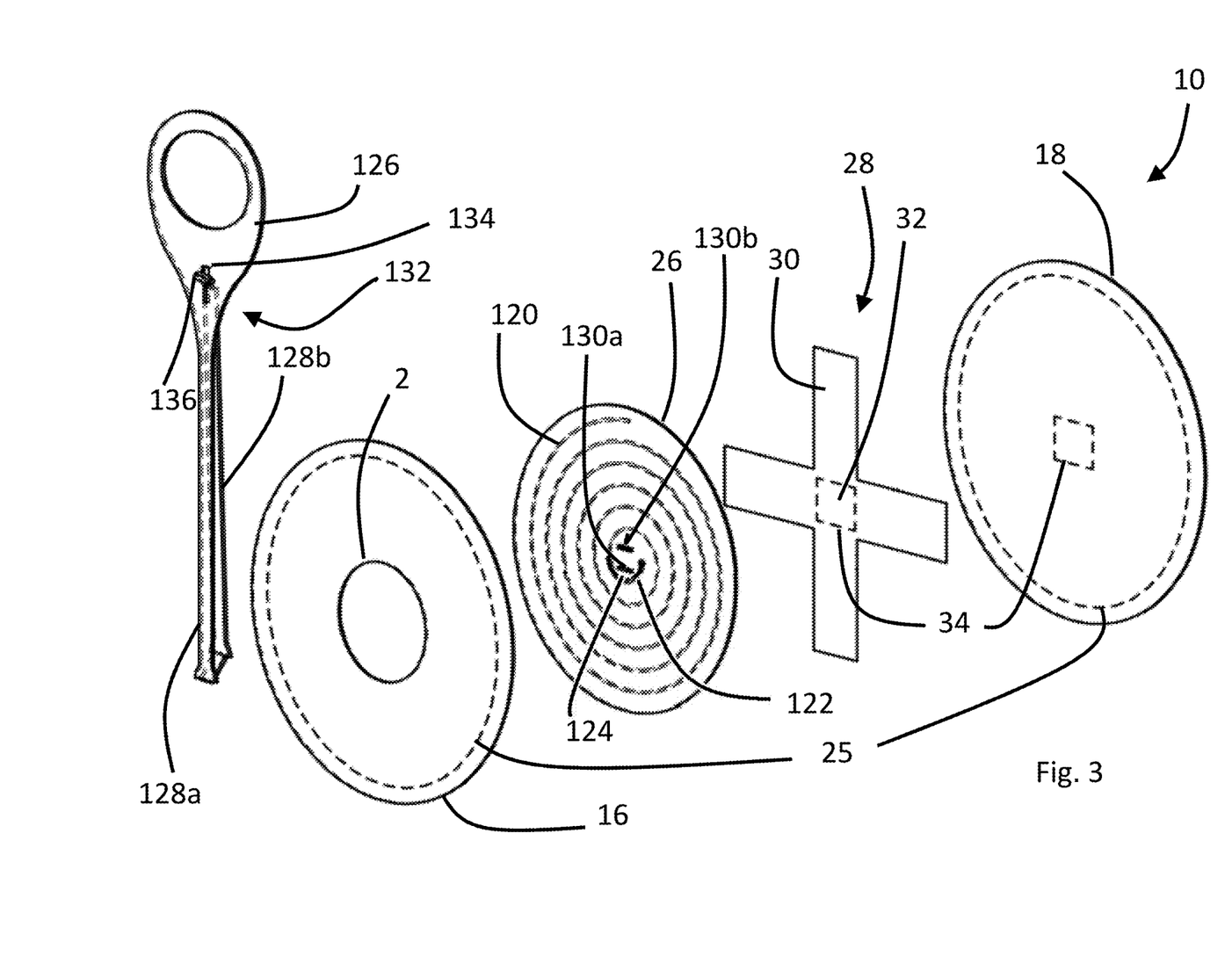
FIG. 3 is an exploded view of the medical device of FIG. 1.

Referring now to the Figures, FIGS. 1-3 illustrate a medical device 10 according to one embodiment disclosed herein. The medical device 10 includes a prosthesis 12 and a deployment device 14. It is noted that commonly-owned U.S. Patent Publication No. 2014/0025093 to Horton et al. (the '093 publication), and commonly-owned and U.S. patent application Ser. No. 61/953,615 to Filipiak et al. (the '615 application), which documents are hereby incorporated by reference in their respective entireties, describe several embodiments for prostheses and deployment devices that are generally applicable to the device 10. That is, the prosthesis 12 and/or the deployment device 14 may be formed according to, or include any combination of features of, any of the embodiments disclosed in the '093 publication and/or the '615 application. In addition to the teachings of these incorporated references, a brief description of the prosthesis 12 and the deployment device 14 is included herein.

Referring again to the illustrated embodiment, the prosthesis 12 includes a first layer 16 and a second layer 18. Due to the orientation during use, e.g., implantation into a cavity of bodily structure of a patient, the first layer 16 may be referred to as the "top" layer and the second layer 18 may be referred to as the "bottom" layer. When implanted, the "top" layer may be in closer proximity to the patient's skin than the "bottom" layer. It is to be understood that prosthesis 12 may be used in any spatial orientation and that the terms "top" and "bottom" are for convenience of discussion only. The top layer 16 may include an opening 20 formed therein, while the bottom layer 18 may be formed as a continuous piece of material. The opening 20 may be any aperture, hole, gap, space, slit, or orifice formed in or by the top layer 16 that provided access into and out of a pocket 22, or cavity or enclosure, formed between the layers 16 and 18. The layers 16 and 18 may be integrally formed from a single piece of folded material and/or secured to each other, e.g., at or proximate to an outer periphery 24, in any desired manner, such as stitching, welding, heat sealing, adhesives, fasteners, etc. For example, according to the illustrated embodiment, the top layer 16 and the bottom layer 18 may be secured together at, near, or along a securement region 25 shown in FIG. 3.

The layers 16 and 18 may be made of any suitable biocompatible material for implantation into a bodily structure of a patient, e.g., in order to assist in repairing a hernia or other defects in the patient. In one embodiment, the layers 16 and 18 may be made of a polypropylene mesh, although it is to be appreciated that any other woven or non-woven implantable material, e.g., known or used for repairing hernias or other defects in a patient's fascia or other bodily structures, may alternatively be used. In one embodiment, the bottom layer 18 may be coated with or otherwise include an anti-adhesion barrier layer, such as the omega-3 fatty acid coating commercialized by Atrium Medical Corp./Maquet Getinge Group and marketed for use with a variety of surgical meshes under the trade name C-QUR. Further examples are described in U.S. Patent Publication No. 2006/0078586, U.S. Pat. No. 8,124,127, U.S. Patent Publication No. 2009/0181937 and U.S. Patent Publication No. 2009/0208552, each of which is incorporated herein by reference in its respective entirety.

The deployment device 14 includes a support member 26 that is initially disposed within the pocket 22 of the prosthesis 12. The support member 26 may be formed from or includes a resilient material that enables the support member 26 to resiliently or springingly urge the prosthesis into a generally flat or planar configuration that facilitates positioning and fixation of the prosthesis 12 at the surgical site during implantation. Additionally, the support member 26 provides a mechanical shield or barrier to protect components of the device 10, e.g., the bottom layer 18, and/or bodily structures of the patient that are located beneath, below, or on the opposite side of the support member 26. For example, a medical professional such a surgeon may need to perform suturing or tacking procedures, and the support member 26 will assist in preventing a needle or tacking tool from inadvertently damaging components or bodily structures located on the opposite side thereof.

In the embodiments disclosed in the '093 publication and '615 application, it is intended for a user to secure the prostheses of those embodiments in place within a patient by tacks, sutures, or other fasteners through their respective top layers. As illustrated in FIGS. 1-3, the medical device 10 includes the top layer 16, which may be used to secure the prosthesis 12 in place within a patient, and additionally includes an affixation element 28 to provide a structure by which alternate, auxiliary, and/or supplemental affixation may be achieved, if desired by a user at the time of implantation. The affixation element 28 is arranged in the pocket 22, located between the bottom layer 18 and the support member 26. In the illustrated embodiment, both the affixation element 28 and the opening 20 are arranged proximate the center of the device 10, as shown. In one embodiment, the opening 20 and at least a portion of the affixation element 28 are aligned to facilitate access to the affixation element 28 via the opening 20.

In the embodiment of FIGS. 1-3, the affixation element 28 includes a plurality of securement tabs 30 extending from a hub region 32. The securement tabs 30 may be any shaped or sized fingers, extensions, projections, legs, arms, spokes, etc. The hub region 32 may be secured to the inner surface of the bottom layer 18 in any desired manner, e.g., via stitching, welds, adhesives, fasteners, etc. The inner surface may alternatively be referred to as an upper surface or a pocket-facing surface. For example, an attachment region 34 is illustrated in FIG. 3, which indicates a location at, along, about, within, or proximate to which the affixation element 28 may be secured to the bottom layer 18 of the prosthesis 12. For example, while the region 34 is illustrated having a square shape, it is to be appreciated that other shapes in this general vicinity may be used, such as an X, a circle, a cross or '+', a zigzag, a straight line or number of lines, or a random or irregular pattern in the area indicated by the region 34.

It is to be appreciated that any number of the tabs 30 may be included. For example, the affixation element 28 is illustrated having four of the tabs 30 extending from the hub region 32, with each of the tabs being relatively long and thin, although a different number of the tabs 30 may be included (e.g., less than or greater than four, such as one, two, three, five, six, etc.) and that any other dimension and/or shape is also contemplated (e.g., longer, thinner, wider, shorter, thicker, rectangular, triangular, oblong, circular, semi-circular, polygonal, etc.). In one embodiment, the affixation element 28 is made of a biocompatible mesh, e.g., similar to that described above with respect to the layers 16 and 18, although it is to be understood that other woven or unwoven biocompatible materials suitable for receiving a suture, tack, or other fastener for implantation in a patient may be used.

Depending on its particular size and arrangement, the support member 26 may initially block access to the affixation element 28 from the opening 20. For example, as shown in FIG. 1, hidden lines are used to illustrate the affixation element 28 located "underneath" or on the opposite side of the support member 26. To this end, the support member 26 may be arranged such that it is capable of being removed from the pocket 22, e.g., thereby enabling the affixation element 28 to be readily accessible via the opening 20. For example, in one embodiment, the support member 26 has an initial (deployed) surface area that is greater than the area of the opening 20, but is reconfigurable in order to be removed from the pocket 22 via the opening 20. In another embodiment, the support member 26 has at least one dimension that is larger than a corresponding dimension of the opening 20 to create an overlap or interference between the inner surface of the first layer 16 and the support member 26, e.g., which frustrates or hinders the removal of the support member 26 from the pocket 22. Examples of particular structure that enable the reconfiguration of the support member 26 are discussed in more detail below and provided in the embodiments disclosed by '093 publication and '615 application incorporated by reference herein. For example, reconfiguration can be accomplished by exerting a sufficiently high tensile force on the support member to force the support member 26 to twist, contort, pull apart, or otherwise change or alter shape in order to be removed through the opening 20.

After access is permitted to the affixation element 28 (e.g., following removal of at least a portion of the support member 28 from the pocket 22), the affixation element 28 provides a structure by which a user can affix or secure the bottom layer 18 of the prosthesis 12 to the fascia or other bodily structure of the patient in which the prosthesis 12 is being implanted. The affixation element 28 may be secured to the bottom layer 16, such that affixing the affixation element 28 to a patient's fascia or other bodily structure will enable a user to position and implant the prosthesis 12 flush against the patient's bodily structure without sagging, drooping, buckling, or unwanted separation of the bottom layer 18 away from the top layer 16 and/or the defect being repaired.

It is to be appreciated that the disclosed and claimed medical devices may include affixation elements having shapes other than the cross or '+' shape of the affixation element 28 shown in FIGS. 1-3. Namely, FIGS. 4-11 illustrate several examples of prostheses having differently sized, shaped, configured, and/or arranged affixation elements, although it is to be understood that these are just a few of the many possible embodiments that those of skill in the art will appreciate in view of the instant disclosure. It is appreciated that the medical device 10 and/or the prosthesis 12 may include the affixation elements of FIGS. 4-11, or features thereof, in lieu of the affixation element 28 shown in FIGS. 1-3. It is also to be understood that while FIGS. 4-11 illustrate only prostheses, that any deployment device (e.g., the deployment device 14) and/or support member (e.g., the support member 26) may be used with these prostheses if desired.

Figures 4, 5:
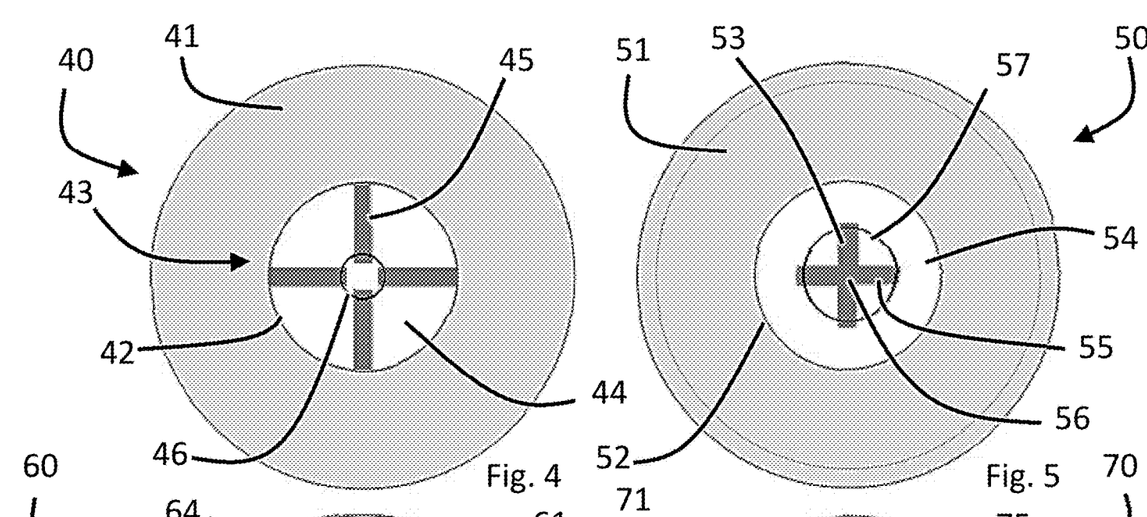
FIGS. 4-11 illustrate prostheses having affixation elements of various shapes, sizes, and arrangements according to several embodiments disclosed herein.

FIG. 4 illustrates a prosthesis 40 having a first (or top) layer 41 with an opening 42 formed therein and an affixation element 43 affixed to a second, or bottom, layer 44. The layers 41 and 44 can be secured to each other similarly to that described above with respect to the layers 16 and 18. The affixation element 43 generally resembles the affixation element 28 of the prosthesis 12 in that it includes a plurality of tabs 45 which can be used, e.g., for assisting in securing the prosthesis 40 to the bodily structure of a patient. Unlike the affixation element 28, the affixation element 43 does not include a hub region. Instead, the tabs 45 are individual or discrete components that are separately secured to the bottom layer 44. The individual tabs 45 of the affixation element 43 may be affixed to the bottom layer 44 at, along, about, within, or proximate to an attachment region 46, e.g., via stitching, welding, adhesives, or any other manner as discussed herein. As shown, the region 46 is located proximate to a center of the device 40 relative to the position of the affixation element 43.

FIG. 5 illustrates a prosthesis 50 having a first (or top) layer 51 with an opening 52 formed therein and an affixation element 53 affixed to a second, or bottom, layer 54. The layers 51 and 54 can be secured to each other similarly to that described above with respect to the layers 16 and 18. The affixation element 53 generally resembles the affixation element 28 in that it includes a plurality of tabs 55 extending from a hub region 56. Unlike the affixation element 28, the affixation element 53 is affixed to the bottom layer 54 via the tabs 55 at, along, about, or proximate to an attachment region 57, e.g., via stitching, welding, adhesives, or any other manner as discussed herein. That is, for example, the outline of the region 57 may be used as a region for stitching the 55 of the affixation element 53 to the bottom layer 54. In this way, the hub region 56 is capable of lifting or separating away from the bottom layer 54, but remains coupled to the bottom layer 54 via the tabs 55. Opposite to the region 46 of the device 40, it is noted that the region 57 is located radially outwardly from the center of the device 50 with respect to the position of the affixation element 53.

Figures 6, 7:
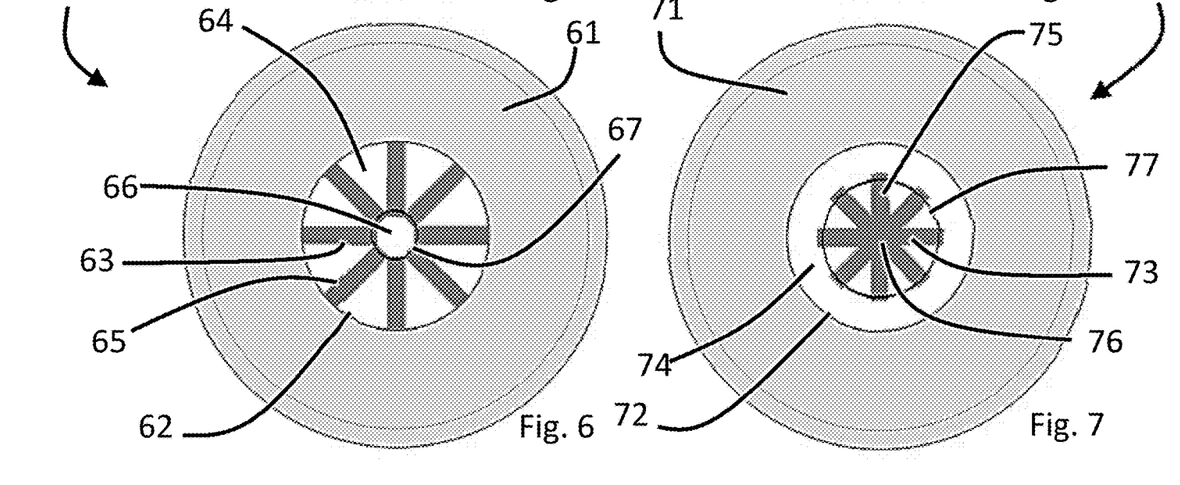

FIG. 6 illustrates a prosthesis 60 having a first (or top) layer 61 with an opening 62 formed therein and an affixation element 63 affixed to a second, or bottom, layer 64. The layers 61 and 64 can be secured to each other similarly to that described above with respect to the layers 16 and 18. The affixation element 63 generally resembles the affixation element 28 in that it includes a plurality of tabs 65 extending from a hub region 66. Additionally, the affixation element 63 is affixed to the bottom layer 64 via the hub region 66 at, along, about, within, or proximate to an attachment region 67, e.g., via stitching, welding, adhesives, or any other manner as discussed herein. Unlike the affixation element 28 illustrated in FIGS. 1-3, the affixation element 63 includes eight tabs 65. As stated above, it is to be appreciated that any number of fingers, extensions, projections, legs, arms, tabs, etc. are contemplated and may be included in other embodiments.

FIG. 7 illustrates a prosthesis 70 having a first (or top) layer 71 with an opening 72 formed therein and an affixation element 73 affixed to a second, or bottom, layer 74. The layers 71 and 74 can be secured to each other similarly to that described above with respect to the layers 16 and 18. The affixation element 73 generally resembles the affixation element 63 in that it includes eight tabs 75 extending from a hub region 76. Unlike the affixation elements 63 and 28, but similar to the affixation element 53, the affixation element 73 is affixed to the bottom layer 74 via the tabs 75 at, along, about, within, or proximate to a region 77, e.g., via stitching, welding, adhesives, or any other manner as discussed herein. In this way, the hub region 76 is capable of lifting or separating away from the bottom layer 74, but remains coupled to the bottom layer 74 via the tabs 75.

Figure 8:
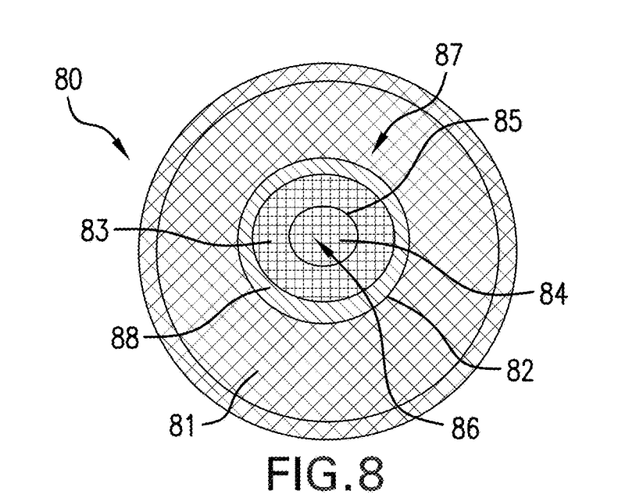

FIG. 8 illustrates a prosthesis 80 having a first (or top) layer 81 with an opening 82 formed therein and an affixation element 83 affixed to a second, or bottom, layer 84. The layers 81 and 84 can be secured to each other similarly to that described above with respect to the layers 16 and 18. Instead of individual fingers, projections, or other extensions or protrusions, the affixation element 83 is ring-shaped having an opening 85 that forms an inner edge 86 of the affixation element 83 that is free or unattached to the bottom layer 84, and an outer edge 87 that is affixed to the bottom layer 84 at, along, about, or proximate to location indicated by a securement region 88. Since the inner edge 86 is not secured to the bottom layer 84, it can be utilized as, and thereby forms, a single, continuous, ring-shaped securement tab. It is noted that the affixation element 83 and/or the opening 85 formed therein may have other shapes, e.g., rectangular, elliptical, oblong, triangular, etc. Additionally in this embodiment, a first pocket is formed between the first layer 81 and the bottom layer 84 and accessible via the opening 82 (e.g., resembling the pocket 22 discussed above), and a second pocket is formed between the affixation element 83 and the bottom layer 84 and accessible via the opening 85.

Figure 9:
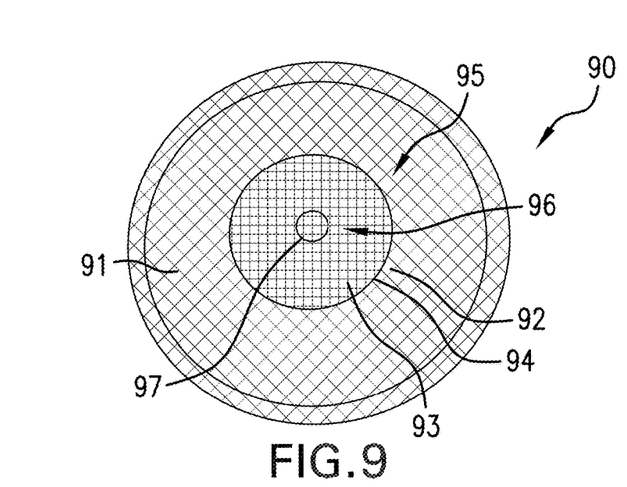

FIG. 9 illustrates a prosthesis 90 having a first (or top) layer 91 with an opening 92 formed therein and an affixation element 93 affixed to a second, or bottom, layer 94. The layers 91 and 94 can be secured to each other similarly to that described above with respect to the layers 16 and 18. Instead of individual fingers, projections, or other extensions or protrusions, the affixation element 93 has a circle shape with an outer edge 95 that is free or unattached to the bottom layer 94, and a center area 96 that is affixed to the bottom layer 94 at, along, about, or proximate to location indicated by a region 97. Since the outer edge 96 is not secured to the bottom layer 94, it can be utilized as, and thereby forms, a single, continuous, circular securement tab. It is noted that the affixation element 93 may have other shapes, e.g., rectangular, elliptical, oblong, triangular, irregular, etc.

Figure 10:
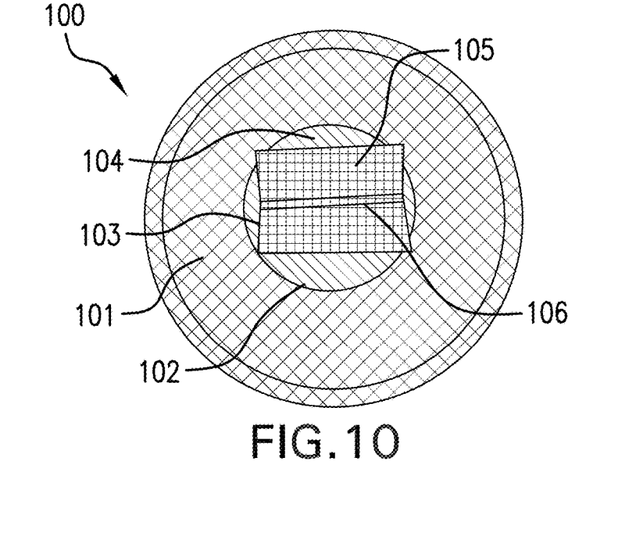

FIG. 10 illustrates a prosthesis 100 having a first (or top) layer 101 with an opening 102 formed therein and an affixation element 103 affixed to a second, or bottom, layer 104. The layers 101 and 104 can be secured to each other similarly to that described above with respect to the layers 16 and 18. The affixation element 103 includes a pair of tabs 105 and is secured to the bottom layer 104 at, along, about, within, or proximate to a region 106, e.g., via stitching, welding, adhesives, or any other manner as discussed herein. The tabs 105 can be formed as halves of a single piece of material that folds or bends at or along the region 106. It is noted that the shape of the tabs 105 does not have to be rectangular, but may be any other shape, e.g., triangular, semi-circular, irregular, etc.

Figure 11:
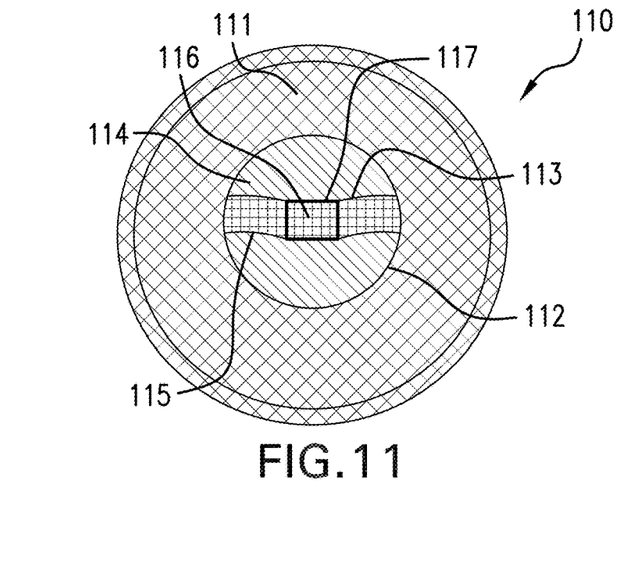

FIG. 11 illustrates a prosthesis 110 having a first (or top) layer 111 with an opening 112 formed therein and an affixation element 113 affixed to a second, or bottom, layer 114. The layers 111 and 114 can be secured to each other similarly to that described above with respect to the layers 16 and 18. The affixation element 113 generally resembles the affixation element 28 in that it includes a plurality of tabs 115 extending from a hub region 116. Additionally, the affixation element 113 is affixed to the bottom layer 114 via the hub region 116 at, along, about, within, or proximate to a region 117, e.g., via stitching, welding, adhesives, or any other manner as discussed herein. Unlike the affixation element 28 illustrated in FIGS. 1-3, the affixation element 63 includes two tabs 115. As stated above, it is to be appreciated that any number of fingers, extensions, projections, legs, arms, tabs, etc. are contemplated and may be included in other embodiments.

The aforementioned '093 publication and '615 application teach a variety of structures that are arranged to undergo reconfiguration for removal from a pocket or enclosure via a relatively smaller sized opening, any of which structures, or features thereof, may be utilized by the support member 26. With specific reference to the illustrated embodiment of FIGS. 1-3, the support member 26 includes a separation line 120 that enables the support member 26 to unravel as discussed in more detail below. It is noted that the separation line 120 may follow any desired path or pattern, and that the spiral pattern shown in merely one example. The separation line 120 may be, for example, a weakened section of material (e.g., a partial through-cut, notch, groove, score, etc.), a previously separated section of material re-attached in a relatively weak or separatable manner (e.g., via a temporary adhesive or breakable or removable fastener(s)), a series of perforations, etc. It is to be understood that the particular embodiment of the support member 26 having the separation line 120 is only one embodiment and that any known or invented structure capable of reconfiguring for removal from the opening 20 may be alternatively included. For example, the support member 26 may be configured to be, or include, one or more bendable or foldable components, e.g., as discussed below with respect to FIGS. 23 and 24, that are capable of the reconfiguration necessary to enable the removal of the support member 26 from the pocket 22 via the opening 20.

The support member 26 may include a through-cut 122 to facilitate initiation of separation along the separation line 120. That is, the through-cut 122 forms a tab 124 for the support member 26 that concentrates forces on or at the separation line 120 when the tab 124 is pulled. For example, the tab 124 may be arranged to act essentially as a short lever arm to create a moment that is applied to the separation line 120 to facilitate initial separation thereof. A user may use their fingers, a pair of forceps, etc., to grip or grab the tab 124 and apply a pulling force thereon, e.g., angled away from the through-cut 122 and back toward the start of the separation line 120, to initiate separation along the separation line 120.

A handle 126 may be included by the deployment device, if desired, to further facilitate initial release and/or positioning of the medical device 10. Pulling on the handle 126 will result in the support member 26 being pulled outwardly with respect to the pocket 22, toward the inner surface of the first layer 16. The inner surface of the first layer 16 may alternatively be referred to or thought of as an underside surface, or pocket-facing surface. The handle 126 may include at least one leg, with two legs, designated as legs 128a and 128b (collectively, the "legs 128") shown in FIGS. 1 and 3. The leg or legs 128 may be coupled to the support member 26 in the general vicinity of the tab 124 and the through-cut 122. To this end, at least one slot, corresponding to the leg or legs 128 is provided. Since there are two legs 128 in the illustrated embodiment, there is accordingly a pair of slots designated with the numerals 130a and 130b (collectively, "the slots 130"), in which slots 130a and 130b the legs 128a and 128b are respectively engaged to couple to the support member 26.

The slots 130a and 130b are positioned such that the slot 130a is located relatively proximate to the through-cut 122, while the slot 130b is located relative distal therefrom. In this way, forces exerted at the location of the slot 130a (e.g., a tensile or pulling force exerted by the leg 128a of the handle 126 coupled to the support member 26 at the slot 130a), will cause the tab 124 to torque or apply a moment on the support member 26 at the start of the separation line 120, while forces exerted at the location of the slot 130b (e.g., a tensile or pulling force exerted by the leg 128b of the handle 126 coupled to the support member 26 at the slot 130b), will be better distributed across the support member 26 and will not cause the same torqueing by the tab 124. Stated alternatively, the force required to initiate separation along the separation line 120 when exerted at or near the location of the slot 130a is significantly less than the force required to initiate separation when exerted at or near the location of the slot 130b. In this way, the handle 126 can be selectively used by a user to either more readily initiate (e.g., via the leg 128a) or prevent (e.g., via the leg 128b) separation along the separation line 120 in response to forces exerted on the support member 26 via the handle 126. It is additionally noted that pulling on both of the legs 128a and 128*b* will also help distribute forces to reduce the likelihood of inadvertent initiation of separation along the separation line. Thus, the handle 126 may form both a positioning tool for the medical device 10 (e.g., when a user applies forces through the leg 128*b* only, or through both the legs 128*a* and 128*b*, in order to move or position the medical device 10 without initiating separation along the separation line) and a removal tool for the support member 26 (e.g., when a user applies forces through the leg 128*a* only in order to initiate separation along the separation line 120), depending on how it is operated by a user.

The handle 126 may include a lock mechanism 132 to selectively lock the legs 128 together. The lock mechanism 132 may include a slot 134 formed in one of the legs 128, e.g., the leg 128*a*, and a widened head 136 formed by the other leg, e.g., the leg 128*b*. The head 136 is wider than the slot 134 such that it cannot be easily removed from the slot 134 without manually rotating the head 136 and pulling the head 136 out of the slot 134. The resiliency of the legs 128 can be selected such that under no loading the head 136 naturally aligns cross-ways with respect to the slot 134 so that such rotation is necessary to transition the legs 128 into an unlocked configuration. When in the locked configuration, pulling forces applied to either of the legs 128 will be better distributed on the support member 26 so as not to inadvertently initiate separation along the separation line. A similar result may be achieved without locking the legs 128, but instead pulling on both of the legs 128 together. It is noted that by making the leg 128*b* shorter than the leg 128*a*, pulling forces applied to the leg 128*a* will be transferred to the leg 128*a* at the lock mechanism 132, and thus exerted on the support member 26 primarily at the location of the slot 130*b*. By releasing the lock mechanism 132 to unlock the legs 128, the leg 128*a* can be readily used to initiate separation along the separation line 120 as discussed above.

A method of using the medical device 10 can be better appreciated in view of FIGS. 12-19. A representative structure 140 is illustrated in FIGS. 12-19 and intended to represent a portion or section of a patient into which the prosthesis 12 of the medical device 10 is to be implanted. Thus, the structure 140 may be any portion of a patient's anatomy, e.g., patient's abdominal region, and is understood to include any tissue/bodily structure into which implantation of the prosthesis may be helpful, e.g., the patient's fascia.

Figure 12:
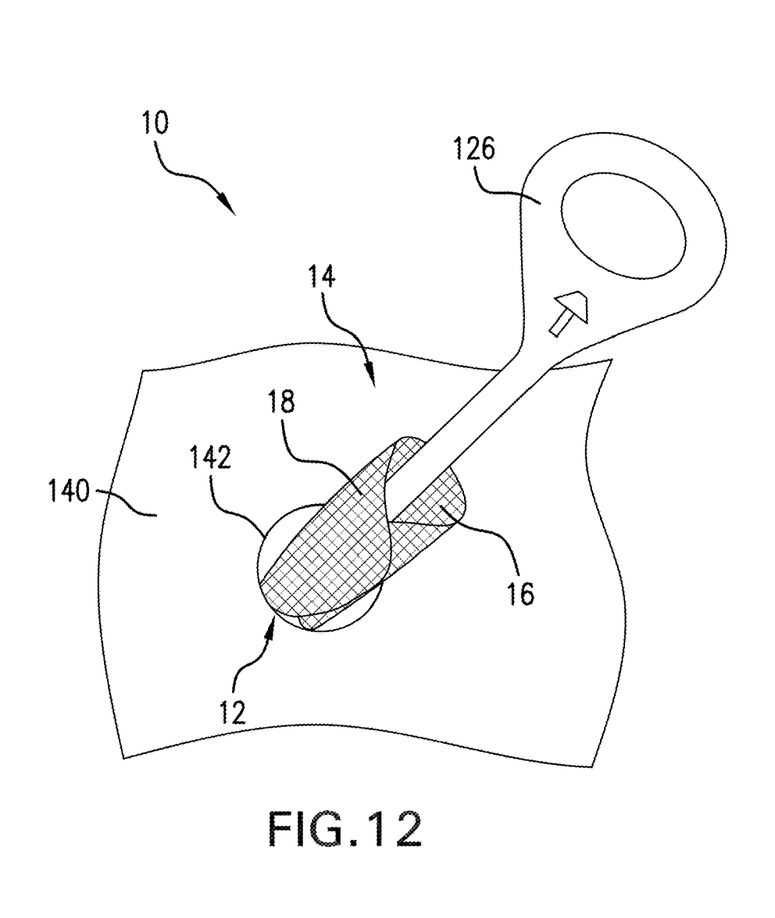
FIGS. 12-19 illustrate various steps of a procedure for using the medical device of FIG. 1 according to one method embodiment disclosed herein.

In FIG. 12, the medical device 10 is illustrated with the prosthesis 12 and the support member 26 in a rolled configuration. When in the rolled configuration, the prosthesis 12 can be inserted into a relatively smaller opening 142 that provides access to an interior cavity of a patient for implantation of the prosthesis 12 within the patient. For example, the opening 142 could be formed as an incision through or into an anatomical structure made by a surgeon or other medical professional proximate to the location of the defect being repaired by implantation of the prosthesis 12.

Figure 13:
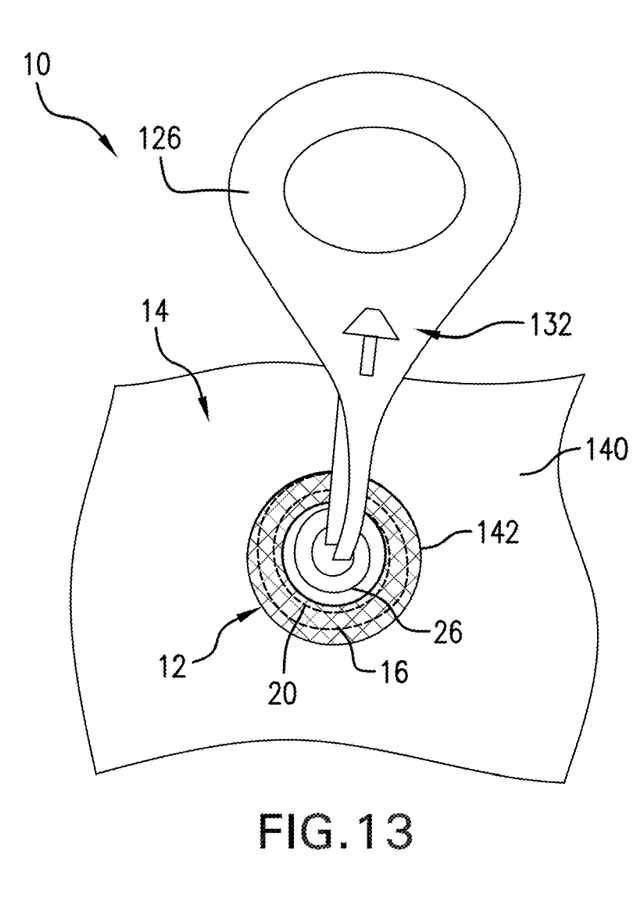
Figure 14:
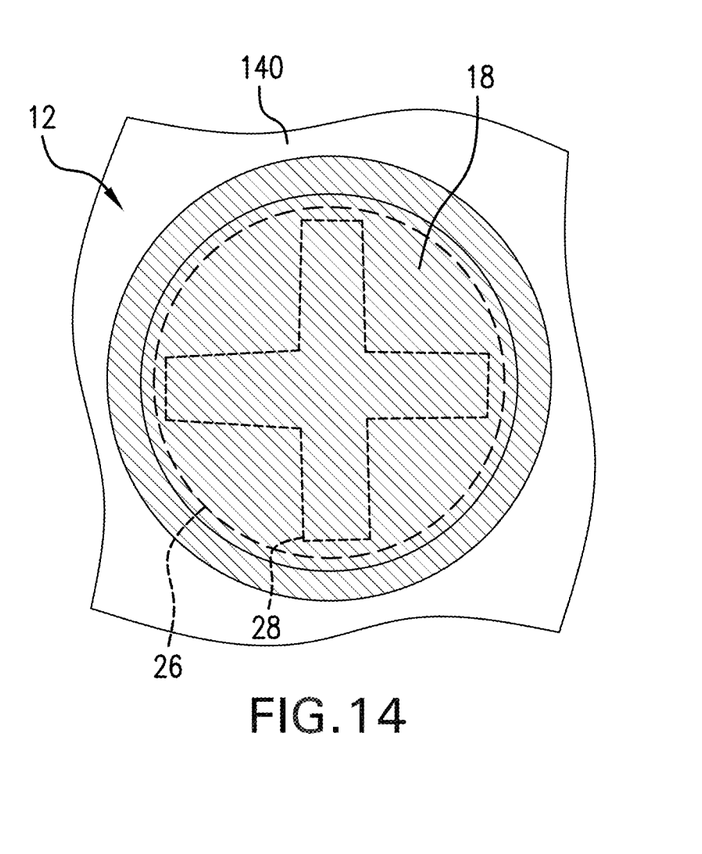

As discussed above, the support member 26 of the deployment device 14 is configured to deploy the prosthesis 12 in a generally radially outward direction back to a generally flat or planar configuration. FIG. 13 illustrates the prosthesis 12 after it has been inserted fully into the opening 142 and permitted to deploy back to its default configuration via the material properties of the support member 26. For example, the support member 26 may be made from flexible, elastically deformable, and/or resilient plastic material. FIG. 14 is a "bottom" view, that is, from the perspective of inside of the patient, of the prosthesis 12 after the prosthesis 12 has been inserted through the opening 142 and deployed to its default configuration by the support member 26.

Figure 15:
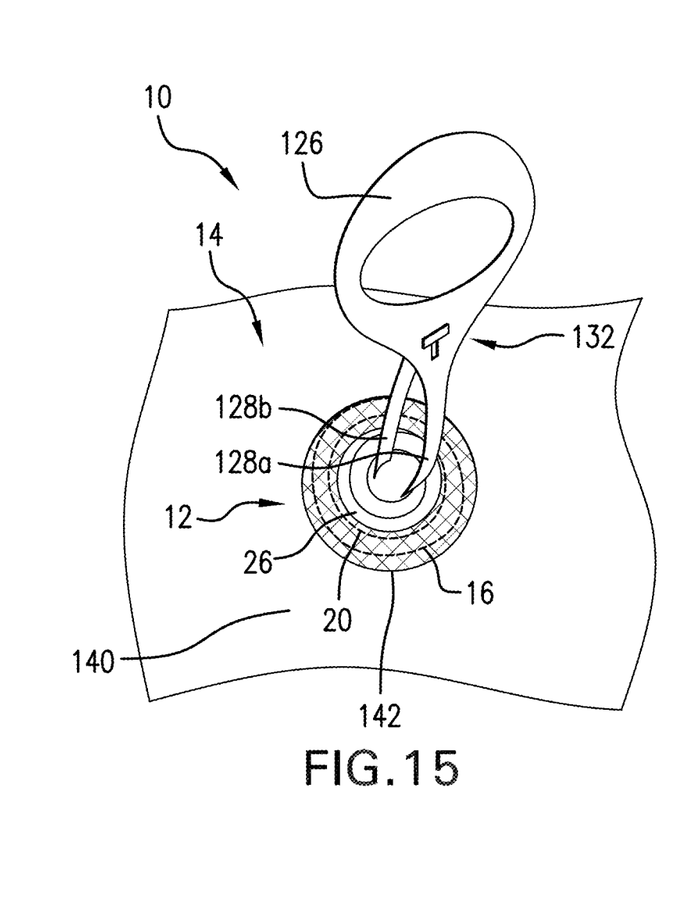

FIG. 15 illustrates the hand of a user, e.g., surgeon or medical professional, positioning the prosthesis by way of the handle 126. The legs 128 of the handle 126 are illustrated in FIG. 15 in the above-discussed locked configuration via engagement of the lock mechanism 132. In this way, the force required to initiate separation along the separation line 120, or otherwise reconfigure the support member 26 for removal will be relatively high and inadvertent removal of the support member 26 unlikely as the user positions the prosthesis 12. Once the prosthesis 12 is suitably positioned, the prosthesis 12 may be secured in place within the bodily structure 140 by tacking, suturing, or otherwise affixing the top layer 16 of the prosthesis to the inner surface of the bodily structure against which the prosthesis 12 is positioned.

Figure 16:
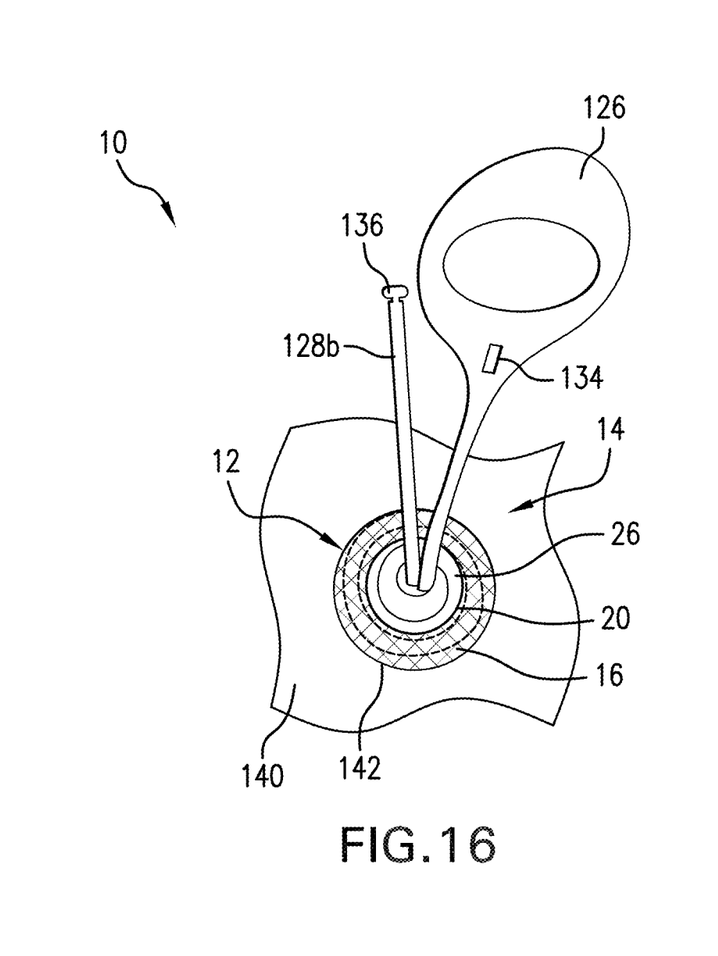
Figure 17:
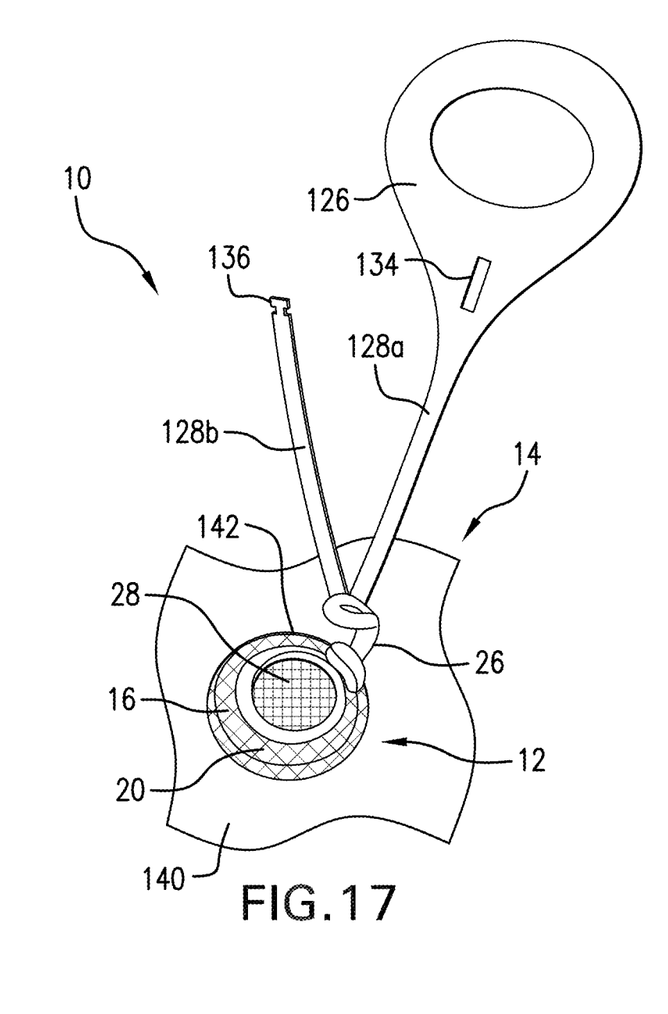

Once the prosthesis is secured in place, the lock mechanism 132 can be released, e.g., by rotating the head 136 and pulling the head 136 through the slot 134, as illustrated in FIG. 16. Once unlocked, pulling forces applied on the handle 126 may be exerted through the leg 128*a* only. As discussed above, the leg 128*a* exerts forces proximate to the slot 130*a*, which results in the tab 124 being lifted by the handle 126 and applying a moment on the separation line 120, thereby enabling separation along the separation line 120 when a suitable pulling force is so exerted. Once separation along the separation line 120 begins, the support member 26 will start to unravel into a continuous strip, and be pulled out through the opening 20 as shown in FIG. 17. This unraveling and removal of the support member 26 reveals the affixation element 28 that was positioning in the pocket 22 beneath the support member 26.

Figure 18:
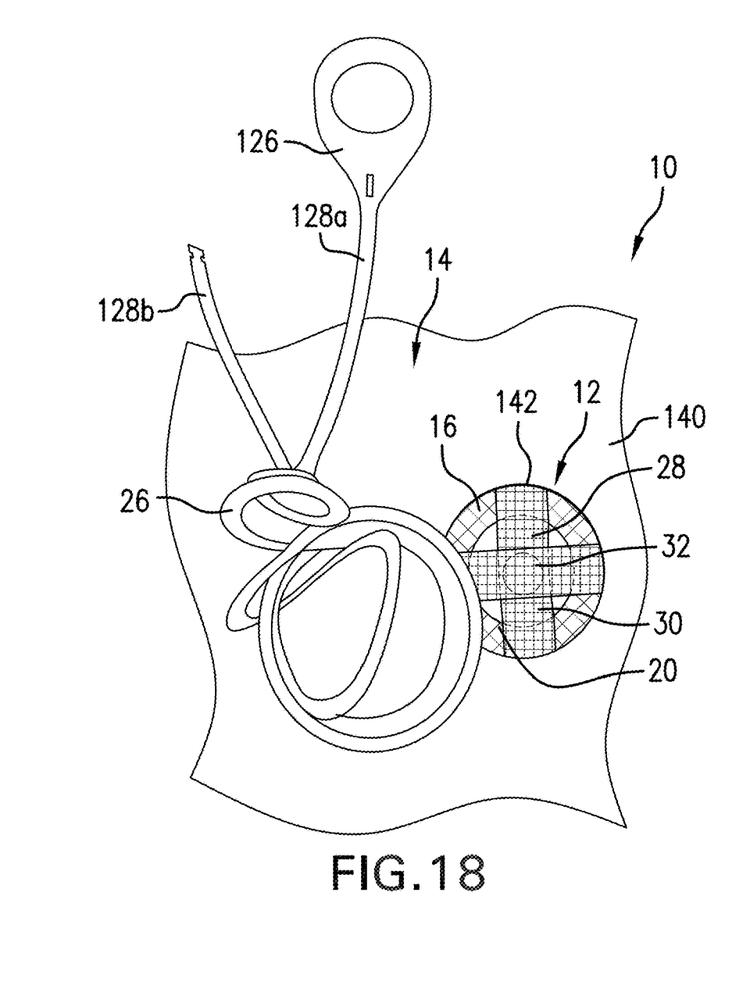
Figure 19:
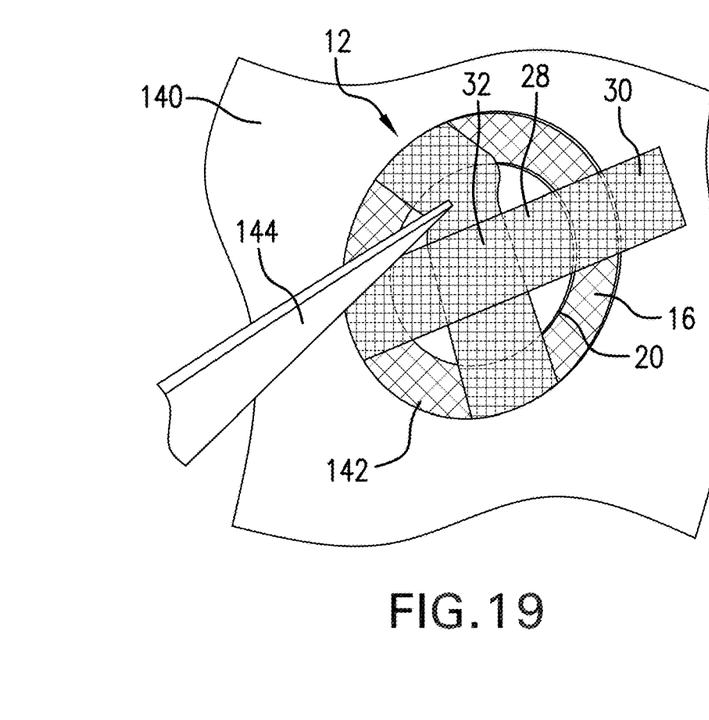

FIG. 18 illustrates the deployment device 14 after the support member 26 is fully unraveled and removed from the prosthesis 12 and the structure 140 via the openings 20 and 142. Once the support member 26 is removed, the affixation element 28 may be accessed via the opening 20. For example, FIG. 19 illustrates a user using a pair of forceps 144 to pull the tabs 30 of the affixation element 28 out of the pocket 22 of the prosthesis. The user may then affix, attach, or secure the tabs 30 to the bodily structure 140, e.g., to the inner surface of the bodily structure 140 and/or to the tissue along the inner wall of the opening 142. Any excess material of the tabs 30 can be folded over or clipped off, and the opening 142 reclosed.

Figure 20:
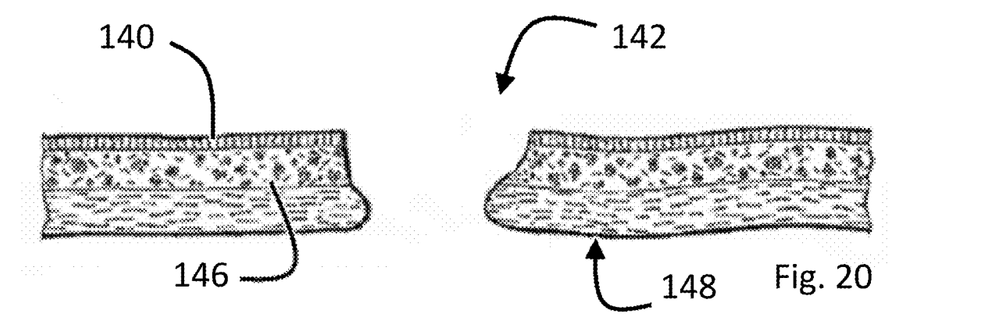
FIGS. 20-22 illustrate cross-sections of various stages of implantation of the prosthesis into a bodily structure.
Figure 21:
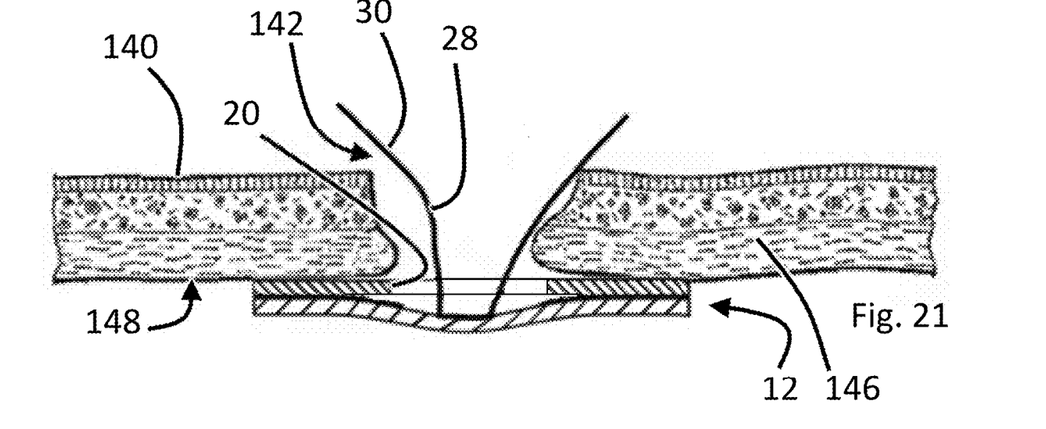
Figure 22:
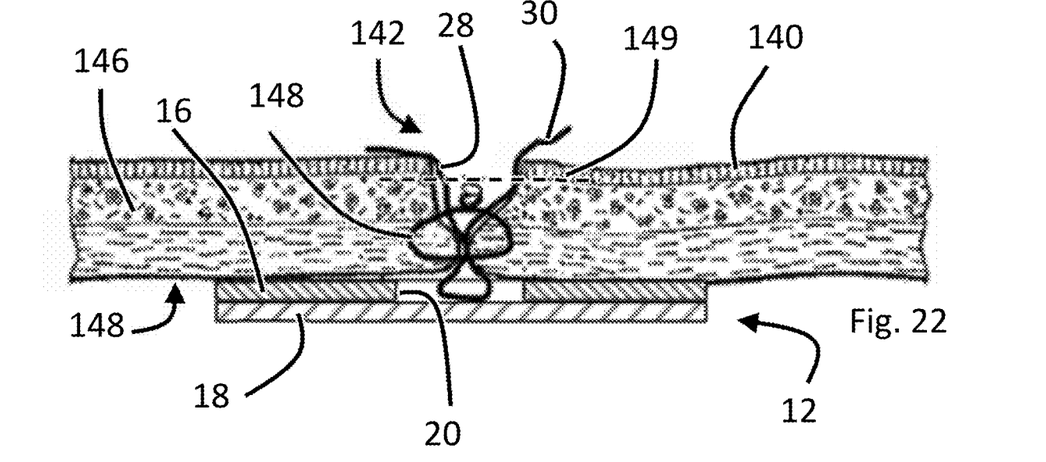

For further clarity, cross-sectional views of the medical device 10 installed in the bodily structure 140 are shown in FIGS. 20-22. It is noted that many of the components of the medical device 10, e.g., the deployment device 14, are not illustrated in FIGS. 20-22 for clarity. The anatomy of the representative bodily structure 140 can also be better appreciated in view of these Figures, which includes several layers of tissue 146. More specifically, FIG. 20 illustrates a cross-section of just the bodily structure 140 having the opening 142 formed therein, before insertion of the prosthesis 12. As described above, the opening 142 may be formed be an incision made into a patient, as well as from a defect in the tissue 146 that is being repaired.

FIG. 21 illustrates a cross-section after the prosthesis has been inserted into a cavity formed by the bodily structure 140. This Figure represents the prosthesis after it has been secured into place, e.g., via sutures, tacks, etc., and the deployment device 14 removed, as the tabs 30 of the affixation element 28 are illustrated extending outwardly through the opening 142. There is noticeable drooping, sagging, or buckling of the bottom layer 18 depicted in FIG.

21, which may occur prior to utilizing the affixation elements 28. It is noted that this drooping, sagging, or buckling, is exacerbated in relatively larger prosthesis due to the increase amount of unsupported material. Without the affixation elements, e.g., the affixation elements 28, described herein, this drooping, sagging, or buckling may result in the undesirable accumulation of fluid, i.e., a seroma. Additionally, it is desirable for the tissue 146 to grow into and around the layers 16 and 18 of the prosthesis 12. The drooping, sagging, or buckling of the bottom layer 18 may frustrate or delay this desired tissue ingrowth.

FIG. 22 illustrates the prosthesis 12 after the tabs 30 of the affixation element 28 have been secured to the bodily structure 140, e.g., via a suture 148, or other fastener, into the tissue 146 lining the walls of the opening 142. As can be better appreciated by comparing FIGS. 21 and 22, the bottom layer 18 can be pulled toward the top layer 16 and supported from the aforementioned drooping, sagging, or buckling, by securing the tabs 30 of the affixation element 28 to the tissue 146. In this way, the prosthesis 12 can be positioning and secured more fully and flushly against and conforming to the contours of an inner surface 148 of the bodily structure 140. After securing the tabs 30 in place to assist in supporting the prosthesis 12, any remaining portion of the tabs 30 may be cut off, e.g., as indicated by a line 149.

Figure 23:
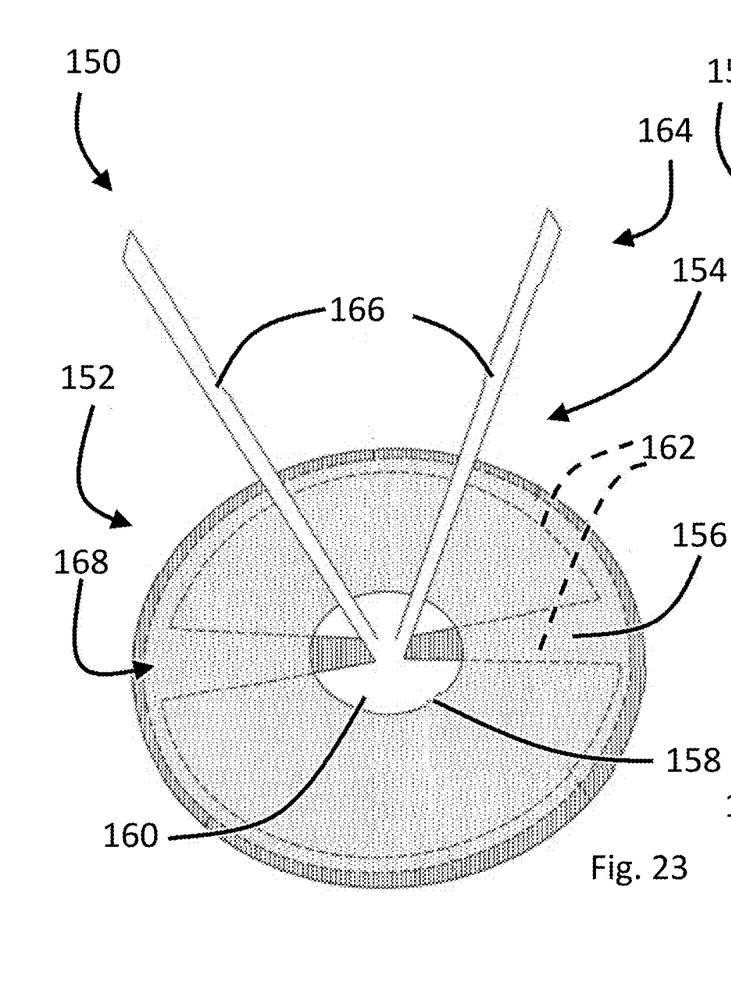
FIGS. 23-24 illustrate a prosthesis according to an embodiment disclosed herein.
Figure 24:
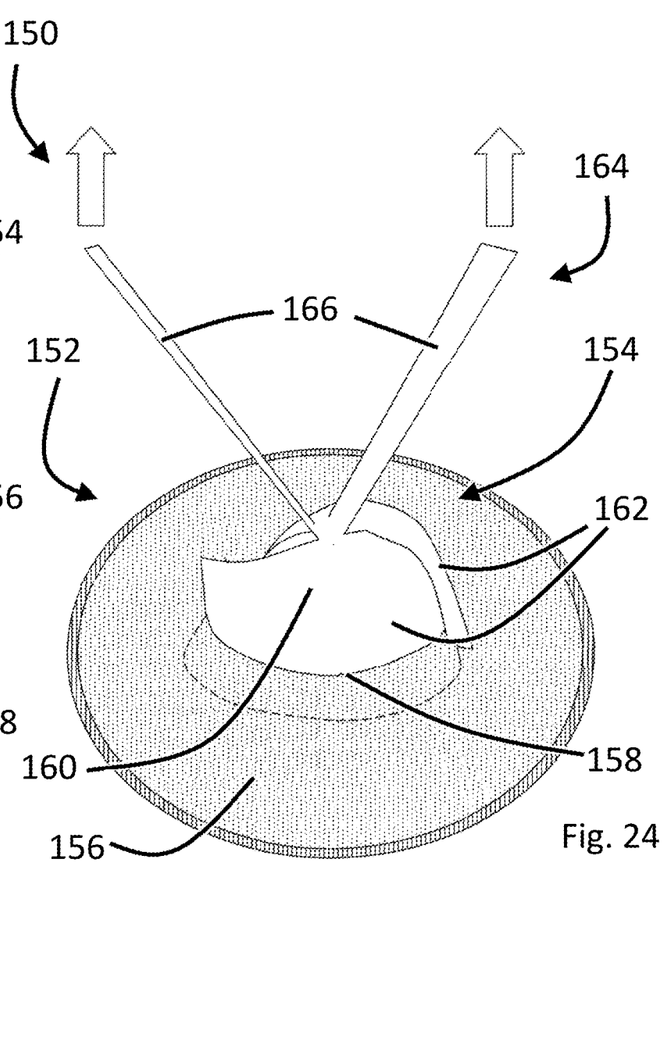

As discussed herein, other support members, deployment devices, and handles may be used or interchanged with those illustrated in FIGS. 1-3. For example, FIGS. 23 and 24 illustrate a medical device 150 according to another embodiment disclosed herein. The medical device 150 includes a prosthesis 152 and a deployment device 154. The prosthesis has top and bottom layers as discussed above with respect to the layers 16 and 18, with a top layer 156 including an opening 158 therein. Unlike the deployment device 14, a support member 160 of the deployment device 154 is formed by two portions 162 that together provide a similar resilient deployment function as the support member 26, e.g., due to material properties of the support member 160. It is to be appreciated that any number of portions 162 may be included. A handle 164 including two legs 166 is coupled to the support member 160. When a pulling force is exerted on the support member 160 via the handle 164, as indicated by arrows in these Figures, the support member 160 is able to undergo a reconfiguration suitable to enable the support member 160 to be removed through the opening 158. That is, a pair of gaps 168 adjacent to the portions 162 enables the support member to reconfigure into a relatively smaller size by bending and/or folding, as illustrated in FIG. 24. Although not illustrated in these Figures, it is understood based on the above description that an affixation element, e.g., the affixation element 28, may be located "beneath" the support member 160 within the pocket formed by the prosthesis 152.

Figures 25, 26, 27:
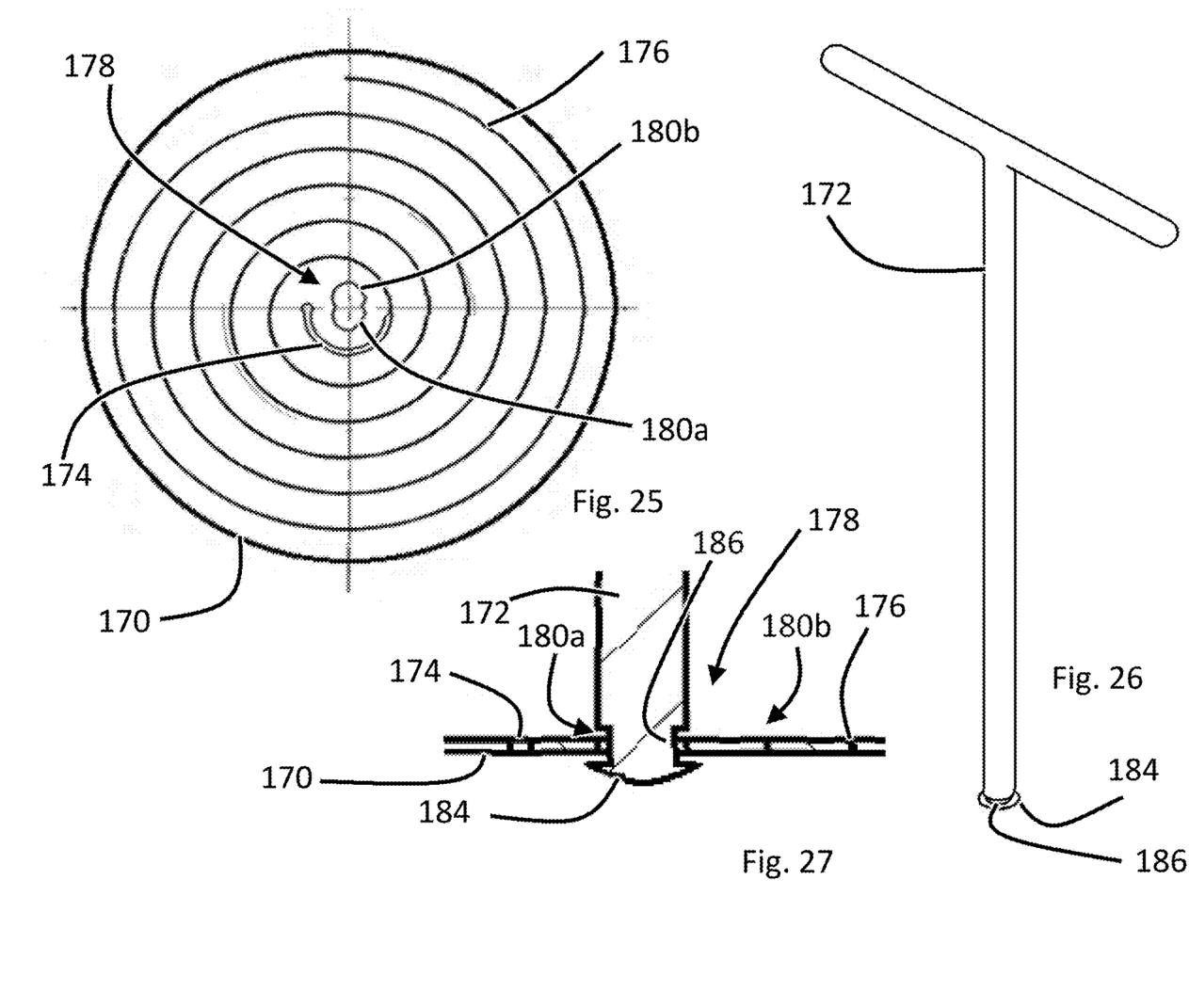
FIGS. 25-27 illustrate an embodiment of a support member, a handle, and a cross-section of a portion of the handle engaged with the support structure, according to an embodiment disclosed herein.

Another example of a deployment device is illustrated in FIGS. 25-27, namely, which includes a support member 170 as illustrated in FIG. 25 and a handle 172 as illustrated in FIG. 26. The handle 172 is illustrated with a generally T-shaped configuration, although it is to be appreciated that it could take other shapes. The support member 170 resembles the support member 26 in several respects, e.g., resilient material composition, a through-cut 174 and a separation line 176, which components resemble in form and function their counterparts from the support member 26. Unlike the support member 26, the support member 170 includes, instead of the slots 130a and 130b, an opening 178 having two circular overlapping portions 180a and 180b (collectively, "the portions 180"). The opening 178 is arranged to receive a connector 182 of the handle 172. The connector 182 may include a head 184, e.g., a flange, cap, shoulder, lip, etc., that is connected to the rest of the handle 172 via a recessed portion 186. The dimensions of the head 184, e.g., the radial dimension, may be selected such that it is greater than the corresponding size of the portions 180 of the opening 178. In this way, for example, after the head 184 is snapped, pressed, squeezed, forced, or otherwise passed or positioned through the opening 178, the relatively larger dimensions of the head 184 prevent, or otherwise frustrate or make more difficult, disengagement of the connector 182 from the opening 178.

The circular portion 180a may be arranged similar to the slot 130a (that is, positioned relatively proximal to the through-cut 174), while the circular portion 180b may be arranged similar to the slot 130b (that is, positioned relatively distal from the through-cut 174). In this way, the handle 172 can function generally similar to the handle 130, in that forces can be more readily applied to the semi-circular flap or tab formed by the through-cut 174 in order to assist in initiating separation along the separation line 176, e.g., into a continuous strip along the path defined by the separation line 172 similar to the discussion of the separation line 120 discussed above. Likewise, similar to the slot 130b, the portion 180b is positioned relatively distal from the through-cut 174. In this way, forces applied to the support structure 170 at the location near the portion 180b are more evenly distributed through the support structure 170. It is thus noted that moving the handle 172 between engagement with the circular portions 180a and 180b results generally in the same functionality as locking and unlocking the lock mechanism 132 as discussed above.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A medical device, comprising:
a first layer having an opening formed therein;
a second layer positioned with respect to the first layer to form a pocket therebetween;
a support member at least partially located in the pocket and reconfigurable to enable removal of the support member from the pocket via the opening; and
an affixation element located in the pocket between the support member and the second layer, and secured directly to a pocket-facing surface of the second layer.

2. The medical device of claim 1, wherein the affixation element is secured to the second layer at a securement region, and the affixation element is secured to the second layer at a location separate from the securement region.

3. The medical device of claim 2, wherein the affixation element is at least partially formed by a mesh material.

4. The medical device of claim 1, wherein the affixation element is at least partially blocked from access through the opening when the support member is located in the pocket.

5. The medical device of claim 1, wherein the affixation element is able to at least partially extend out from the pocket through the opening when the support member is removed from the pocket.

6. The medical device of claim 1, wherein the medical device can be held against an anatomical structure by the support member when the support member is at least partially located within the pocket, and by the affixation element when the support member is fully or at least partially removed from the pocket.

7. The medical device of claim 1, wherein the pocket is delimited by an underside surface of the first layer and the pocket-facing surface of the second layer.

8. The medical device of claim 7, wherein a tensile force is able to be applied to the medical device at (i) the underside surface of the first layer by the support member and (ii) at the pocket-facing surface of the second layer by the affixation element.

9. The medical device of claim 1, wherein the support member has at least one dimension that is larger than a corresponding dimension of the opening to frustrate or impede removal of the support member from the pocket.

10. The medical device of claim 9, wherein the support member is reconfigurable in response to a tensile force applied to the support member in order to remove the support member from the pocket via the opening.

11. The medical device of claim 1, wherein the affixation element includes one or more tabs extending from a hub and the hub is affixed to the pocket-facing surface of the second layer.

12. The medical device of claim 1, wherein the affixation element has a circular shape or a polygonal shape.

13. The medical device of claim 1, wherein the affixation element includes separate fingers or tabs that are secured individually to the pocket-facing surface of the second layer.

14. The medical device of claim 1, wherein the affixation element is attached to the pocket-facing surface of the second layer at a region located generally proximate to a center of the medical device relative to a position of the affixation element.

15. The medical device of claim 1, wherein the affixation element is attached to the pocket-facing surface of the second layer at a region located generally radially outwardly from a center of the medical device relative to a position of the affixation element.

16. The medical device of claim 1, wherein the affixation element is secured to the pocket-facing surface of the second layer by a component selected from the group consisting of stitching, a weld, an adhesive, and a fastener.

17. A method of implanting a medical device comprising the steps of:
  positioning a medical device against an anatomical structure by exerting a tensile force on a support member of the medical device, the support member at least partially located in a pocket formed between a first layer and a second layer of the medical device that are secured to each other, and the support member extends outward from the pocket through an opening in the first layer;
  removing the support member from the pocket through the opening in the first layer in order to provide access through the opening to an affixation element located in the pocket and secured directly to a pocket-facing surface of the second layer; and
  securing the medical device to the anatomical structure via the affixation element in order to prevent substantial drooping, sagging or buckling of the medical device positioned against the anatomical structure.

18. The method of claim 17, wherein removing the support member from the pocket includes reconfiguring the support member via the tensile force to fit the support member through the opening.

19. A medical device, comprising:
  a first layer having an opening formed therein;
  a second layer positioned with respect to the first layer to form a pocket therebetween;
  a support member at least partially located in the pocket and reconfigurable to enable removal of the support member from the pocket via the opening, wherein the support member is formed with a separation line and has a through-cut disposed to facilitate initiation of separation the separation line, and the through-cut forms a tab that concentrates force on or at the separation line when pulled; and
  an affixation element located in the pocket between the support member and the second layer, and secured directly to a pocket-facing surface of the second layer.

20. The medical device of claim 19, wherein the affixation element comprises a plurality of tabs extending from a hub region.

* * * * *